US008697131B2

(12) United States Patent
Tuereli et al.

(10) Patent No.: US 8,697,131 B2
(45) Date of Patent: *Apr. 15, 2014

(54) METHOD FOR PRODUCING PHARMACEUTICAL DRUG PARTICLES OF SMALL PARTICLE SIZE

(75) Inventors: Akif Emre Tuereli, Saarbruecken (DE); Bernd Penth, Lebach (DE); Peter Langguth, Nieder-Olm (DE); Bernd Baumstuemmler, Saarlouis (DE)

(73) Assignee: Instillo GmbH, Saarlouis (DE)

( * ) Notice: Subject to any disclaimer, the term of this patent is extended or adjusted under 35 U.S.C. 154(b) by 199 days.

This patent is subject to a terminal disclaimer.

(21) Appl. No.: 13/138,389

(22) PCT Filed: Feb. 11, 2010

(86) PCT No.: PCT/DE2010/075015
§ 371 (c)(1),
(2), (4) Date: Aug. 10, 2011

(87) PCT Pub. No.: WO2010/091683
PCT Pub. Date: Aug. 19, 2010

(65) Prior Publication Data
US 2011/0294770 A1    Dec. 1, 2011

(51) Int. Cl.
*A61K 9/14*    (2006.01)
*A61K 9/127*    (2006.01)
*B01J 13/02*    (2006.01)

(52) U.S. Cl.
USPC .......................................... 424/489; 264/4.6

(58) Field of Classification Search
CPC .......... A61K 9/14; A61K 9/16; A61K 9/1682
See application file for complete search history.

(56) References Cited

U.S. PATENT DOCUMENTS

| | | |
|---|---|---|
| 5,314,506 A | 5/1994 | Midler, Jr. et al. |
| 6,074,441 A | 6/2000 | Schulte et al. |
| 6,558,435 B2 | 5/2003 | Am Ende et al. |
| 7,041,144 B2 | 5/2006 | Kozyuk |
| 2003/0206959 A9 | 11/2003 | Kipp et al. |
| 2004/0173139 A1 | 9/2004 | Kozyuk |
| 2005/0139144 A1 | 6/2005 | Muller et al. |
| 2008/0279928 A1 | 11/2008 | Moschwitzer |
| 2009/0297565 A1 | 12/2009 | Müller et al. |

FOREIGN PATENT DOCUMENTS

| | | |
|---|---|---|
| DE | 196 17 085 | 10/1997 |
| DE | 102 14 031 | 2/2004 |
| DE | 10 2005 011 786 | 9/2006 |
| DE | 10 2005 017 777 | 10/2006 |
| DE | 10 2005 048 021 | 4/2007 |
| DE | 10 2005 053 862 | 5/2007 |
| EP | 1 165 224 | 1/2002 |
| EP | 1 652 515 | 5/2006 |
| WO | WO 00/38811 | 7/2000 |
| WO | WO 00/61275 | 10/2000 |
| WO | WO 02/055059 | 7/2002 |

OTHER PUBLICATIONS

International Search Report of PCT/DE2010/075015, Aug. 13, 2010.

*Primary Examiner* — Carlos Azpuru
(74) *Attorney, Agent, or Firm* — Collard & Roe, P.C.

(57) ABSTRACT

Pharmaceutical drug particles of small particle size are produced by combining a solvent-non-solvent precipitate with an in-situ spray drying process. A pharmaceutical drug is dispersed in a water-miscible solvent, in particular ethanol, and heated in an infeed line under pressure to above the boiling point of the solvent until the drug dissolves. This solution collides as a fine liquid jet with a fine water jet in a gas-permeated microreactor, and the fine mist so arising vaporises rapidly. The organic solvent vaporizes first, then the water. The water may contain surface modifiers.

3 Claims, 1 Drawing Sheet

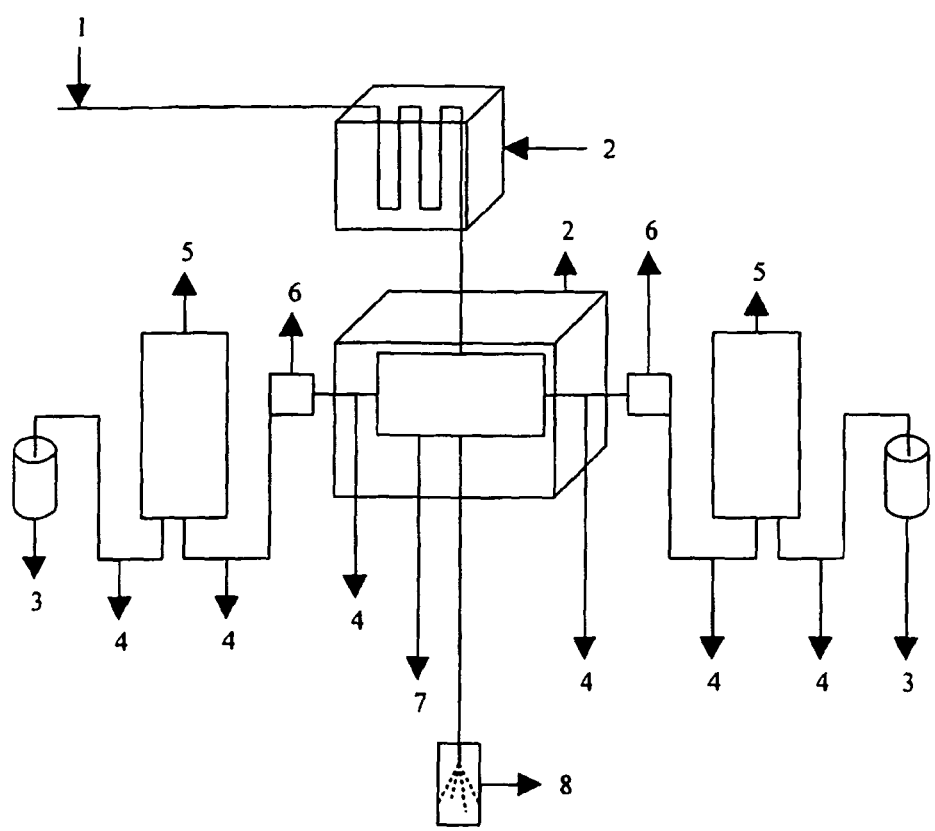

* # METHOD FOR PRODUCING PHARMACEUTICAL DRUG PARTICLES OF SMALL PARTICLE SIZE

CROSS REFERENCE TO RELATED APPLICATIONS

This application is the National Stage of PCT/DE2010/075015 filed on Feb. 11, 2010, which claims priority under 35 U.S.C. §119 of German Application No. 10 2009 008 478.9 filed on Feb. 11, 2009, the disclosure of which is incorporated by reference. The international application under PCT article 21 (2) was not published in English.

BACKGROUND OF THE INVENTION

This invention relates to a method for producing pharmaceutical drug particles of small particle size.

The patent applications US 2003/0206959, U.S. Pat. Nos. 5,314,506, 6,558,435, 7,041,144, DE 102 14 031, DE 10 2005 017 777, DE 10 2005 053 862, DE 10 2005 011 786 and DE 196 17 085 describe a series of pharmaceutical drugs that dissolve poorly in water and methods of obtaining the drugs in nanoscale form in order to increase their bioavailability.

WO 00/38811 A1 describes an apparatus and process for preparing crystalline particles, which involves precipitation induced by ultrasonic radiation.

WO 02/055059 A2 describes a method of preparing submicron pharmaceutically active compounds, which involves dissolving a first quantity of the pharmaceutically active substance in a water-soluble first organic solvent, mixing the resulting solution with a second solvent in order to precipitate the pharmaceutically active substance, and seeding the first solution or the second solvent or the mixture of the solution with the second solvent.

The US 2004/0173139 A1 describes a device and process for crystallizing a compound by means of hydrodynamic cavitation.

EP 1 652 515 A1 discloses a method of producing ultramicroparticles, which involves first dissolving a substance in a good solvent, then mixing the solution with a second solvent in which the substance dissolves poorly, and finally subjecting the resulting mixture to emulsification under a specified pressure.

SUMMARY OF THE INVENTION

The object of this invention was to provide a method of producing even smaller particles.

This method refers to the production of the drugs described there and mentioned by name, but is not limited to these. It can be used with all other pharmaceutical drugs that dissolve poorly in water.

The particles of the invention are obtained by combining a solvent/non-solvent drug precipitation with an in-situ spray vaporisation of the solvent in the presence of a surface modifier.

To this end, the pharmaceutical drug is first dissolved in a water-miscible organic solvent such as ethanol, and a surface modifier is then dissolved in the solution.

A pump is used to inject the solution via a pipe under raised pressure of up to more than one bar, better up to more than 10 bar, even better up to more than 50 bar, through a nozzle into the precipitation reactor. The nozzle of the precipitation reactor serves simultaneously as pressure regulating valve. The supply pipe, or infeed line, can be heated from the exterior, either by means of an electric resistance heater or by a heating bath, said infeed line preferably being of spiral configuration.

A second pump is used to inject the non-solvent—preferably water—in the same way via a pipe and under raised pressure through a second nozzle into the precipitation reactor. This infeed line, too, can be heated from the exterior, either by means of an electric resistance heater or by a heating bath, said infeed line preferably being of spiral configuration.

The precipitation reactor is a microreactor which is preferably designed as described in EP 1165224. Nitrogen is used with preference as gas.

Collision of the drug—liquid jet with a water jet causes non-solvent precipitation and the formation of a fine mist. In this way, the solvent is vaporised from the solvent/non-solvent mixture practically simultaneously with non-solvent precipitation. It is not necessary for the temperature of the solvent/non-solvent mixture to be higher than the solvent's vaporization temperature.

On account of the high back pressure of the liquids in front of the nozzles, the resulting high jet speeds of the colliding liquid jets and hence the fineness of the mist droplets, but also on account of the elevated temperature of at least one of the liquid jets and of the additional flushing of the reactor with air, warm air, hot air or, better, an optionally pre-heated inert gas such as nitrogen, the solvent vaporizes very quickly, making for the formation of very small, coated drug particles.

The solution, in the form of a fine, heated liquid jet of solvent, is thus made to collide with at least one second heated liquid jet comprising water in a gaseous atmosphere.

The speed of the liquid jets is usually more than 1 m/s; at a pressure in excess of 50 bar, it is even more than 50 m/s.

At the collision point of the at least two jets, very fast solvent/non-solvent precipitation occurs. The rapid mixing causes a very high level of supersaturation and produces a large number of nuclei, which are subsequently unable to grow much because only little dissolved drug is available.

Ostwald ripening, the phenomenon by which smaller particles disappear as larger particles grow, does not occur with the method described because the necessary residual solubility of the precipitated particles in the solvent/non-solvent mixture has already been eliminated by the in-situ vaporisation of the solvent fraction from the solvent/non-solvent mixture within an extremely short period following precipitation of the particles.

In an extended embodiment, pharmaceutical drugs which are only moderately soluble in the solvent can be prepared as a dispersion and heated until they dissolve before they are supplied to the reactor. A pharmaceutical drug may also be dissolved by passing it through a heated reactor infeed line in which the temperature of the pressurized solvent rises above the boiling point of the solvent at room temperature. This procedure shortens the period during which thermosensitive drugs need to be heated.

It is to advantage for the collision point to be located in a moving stream of gas.

The collision point is expediently located in a duct that widens in the direction of the flowing gas. Particularly where higher pressures are used to form the liquid jets, very small, fog-like aerosol droplets form from which, on account of their large surface area, at least the more volatile solvent fractions vaporise very quickly, generating the pharmaceutical drug either as a dispersion or, depending on the temperature of the liquids and of the gas and on their throughputs, as powder, in a manner similar to spray-drying.

It is to advantage for the gas stream and the microreactor, as well as the infeed lines for solvent and non-solvent, to be heated. The temperature is selected such that no thermal damage is done to the pharmaceutical product.

The minimum particle size obtainable with this method is substantially below the particle sizes obtainable with prior art methods.

Ethyl alcohol or acetone are well suited as solvents. However, other volatile water-miscible solvents such as methanol, isopropanol or tetrahydofuran are also possible.

Highly suitable reactors include those described in DE 10 2005 048 201. However, other "free jet reactors" where free, liquid jets collide in a gaseous zone may also be considered.

It is also possible, but usually less favourable, for the jets not to collide directly but to impinge upon the chamber walls of a gas-permeated chamber and to be mixed by way of the resulting turbulence.

Suitable gases include all gaseous elements, especially inert gases, but also dried air, nitrogen or carbon dioxide.

BRIEF DESCRIPTION OF THE DRAWINGS

FIG. 1 shows the structure of the device according to the invention. 1: Gas supply, 2: water bath, 3: solvent tank, 4: infeed lines, 5: pump, 6: filter, 7: reactor, 8: collecting tank, 9: antisolvent tank

DETAILED DESCRIPTION OF THE EMBODIMENTS

EXAMPLE 1

The active ingredient gliclazide and the polymer Eudragit S100 were dissolved in methanol to give an overall concentration of 2 mg/ml and a polymer:drug ratio of 200:1. To prepare the nanoparticles, an operating pressure of 0.1 bar was set for the stream of nitrogen gas, flow rates of 0.5, 2.5 and 10 ml/min set for the methanol containing drug and polymer, and a flow rate of 10 ml/min for the water used as anti-solvent.

High drug-load levels (92.0, 97.6%) were obtained with the polymer:drug ratio set at 200 and an anti-solvent:solvent flow-rate ratio of greater than 5.

EXAMPLE 2

Nanoparticles were prepared as described in example 1 but using danazol as drug, hydroxypropyl methylcellulosephthalate as polymer and acetone as solvent. High drug-load levels of up to 100% were obtained by selecting a polymer:drug ratio of 20, irrespective of the anti-solvent:solvent flow rate ratio.

EXAMPLE 3

Nanoparticles were prepared as described in example 1, but with a polymer:drug ratio of 200 at temperatures of 40, 60, 60 and 100° C. and nitrogen operating pressures of 0.1 bar and 1 bar. It was observed that increasing the temperature or pressure led to an increase in nanoparticle size. It was possible to produce nanoparticles ranging in size from 205 to 756 nm by varying these parameters.

EXAMPLE 4

Nanoparticles were prepared as described in example 2, but with a polymer:drug ratio of 20 at temperatures of 40, 60, 60 and 100° C. and nitrogen operating pressures of 0.1 bar and 1 bar. It was observed that increasing the temperature or pressure led to an increase in nanoparticle size. It was possible to produce nanoparticles ranging in size from 30 to 275 nm by varying these parameters.

EXAMPLE 5

Nanoparticles were prepared as described in example 1 using a polymer:drug ratio of 200 and different total-solids concentrations of 2, 3, 5 and 8 mg/ml in methanol, acetone or tetrahydrofuran. It was observed that increasing the total-solids content led to an increase in nanoparticle size. With the different solvents, the average particle size increased in the order MeOH>THF>acetone. It was possible to produce nanoparticles ranging in size from 70 to 300 nm by varying these parameters.

EXAMPLE 6

Nanoparticles were prepared as described in example 2 using a polymer:drug ratio of 50 and different total-solids concentrations of 3, 5 and 8 mg/ml in acetone:ethanol 50:50 (w/w) or ethanol:water 90:5 (w/w) mixtures. It was observed that increasing the total-solids content led to an increase in nanoparticle size. With the different solvent mixtures, the average particle size increased in the order EtOH:water>acetone:EtOH. It was possible to produce nanoparticles ranging in size from 38 to 325 nm by varying these parameters.

The invention claimed is:

1. Method for producing pharmaceutical drug particles of small particle size, comprising the following steps:

Dissolving pharmaceutical drug particles in a water-miscible solvent

Pumping the thus-prepared dispersion under raised pressure through a dispersion conveyor line at the end of which a nozzle that functions as a pressure regulator is located Dissolving the drug particles by heating the dispersion conveyor line to a temperature above the boiling point of the solvent at normal pressure to create a drug solution, Passage of the drug solution through the nozzle of a precipitation/spray-drying reactor Collision of the liquid jet of drug solution with a liquid jet formed by another nozzle of the precipitation/spray-drying reactor, the latter jet consisting of water or an aqueous solution Maintenance of a gaseous atmosphere at the collision point of the liquid jets by supplying gas to blow the precipitation zone free, or by at least partial vaporisation of solvent and water in the collision zone as a result of the pressure drop following the passage of the jets through the respective nozzles, or, where a free-jet reactor is used, by gravity-based removal of the dispersion mist Extremely rapid mixing due to mixing taking place in the form of impinging jets in a gaseous atmosphere, with a mixing time of less than 100 ms, preferably less than one ms Formation of nanoparticulate nuclei by very fast diffusion-controlled solvent/non-solvent precipitation at the collision point and the plate-like mixing zone of the liquid jets in a gaseous atmosphere.

2. Method according to claim 1, wherein the dispersion conveyor line has an additional, pump-fed input for pure solvent, the temperature of the solvent being higher than the solvent's boiling point at normal pressure and higher than the temperature of the dispersion conveyor line, thus causing rapid solution of the remaining still-undissolved dispersed particles in the dispersion being conveyed and reducing the time during which the drug is under thermal stress.

3. Method according to claim 1, wherein the latter jet consists of an aqueous solution containing biocompatible constituents that modify the surface of the ultrafine particles formed during precipitation.

* * * * *